US00PP30031P2

(12) United States Plant Patent
Van Swieten

(10) Patent No.: US PP30,031 P2
(45) Date of Patent: Dec. 25, 2018

(54) ***PHALAENOPSIS* ORCHID PLANT NAMED 'PHALDOQZI'**

(50) Latin Name: ***Phalaenopsis* hybrid**
Varietal Denomination: PHALDOQZI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,061

(22) Filed: Sep. 11, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALDOQZI', particularly characterized by having white, dotted flowers, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALDOQZI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDOQZI'.

The new *Phalaenopsis* plant is a product of a planned breeding program conducted by the inventor in Bleiswijk, The Netherlands. The objective of this breeding program was to create a new *Phalaenopsis* plant with numerous attractive and unique white, dotted flowers, suitable for potted plant production.

The new *Phalaenopsis* plant 'PHALDOQZI' is a result of cross-pollination made by the inventor in March 2005 in Bleiswijk, The Netherlands of the proprietary female, or seed parent, *Phalaenopsis* hybrid '01-5021' (unpatented) with the proprietary male, or pollen parent, *Phalaenopsis* hybrid '22884-01' (unpatented).

The new *Phalaenopsis* was selected by the inventor as a single plant within the progeny of the stated cross-pollination in a controlled greenhouse in Bleiswijk, The Netherlands in March 2008. Asexual reproduction of the new *Phalaenopsis* plant by meristem tissue culture since 2010 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALDOQZI' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDOQZI' as a new and distinct variety of *Phalaenopsis* plant.

1) White, dotted flowers;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in July 2017. Colors in the photographs may differ from the color values cited in the detailed botanical description, which accurately describe the actual colors of the new variety.

DESCRIPTION OF THE NEW VARIETY

Figure 1:
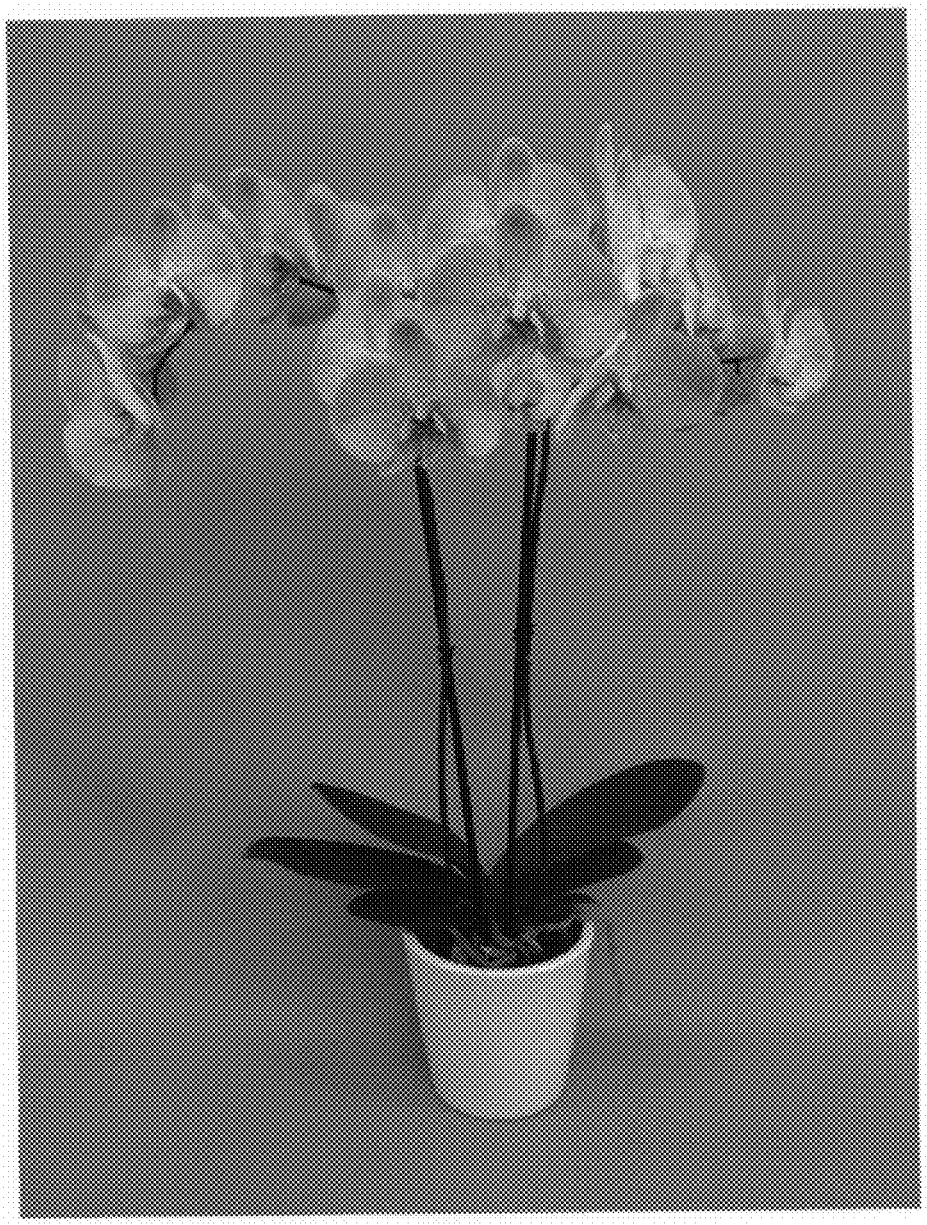
FIG. 1 shows the overall plant habit, including blooms and foliage of 'PHALDOQZI'.
Figure 2:
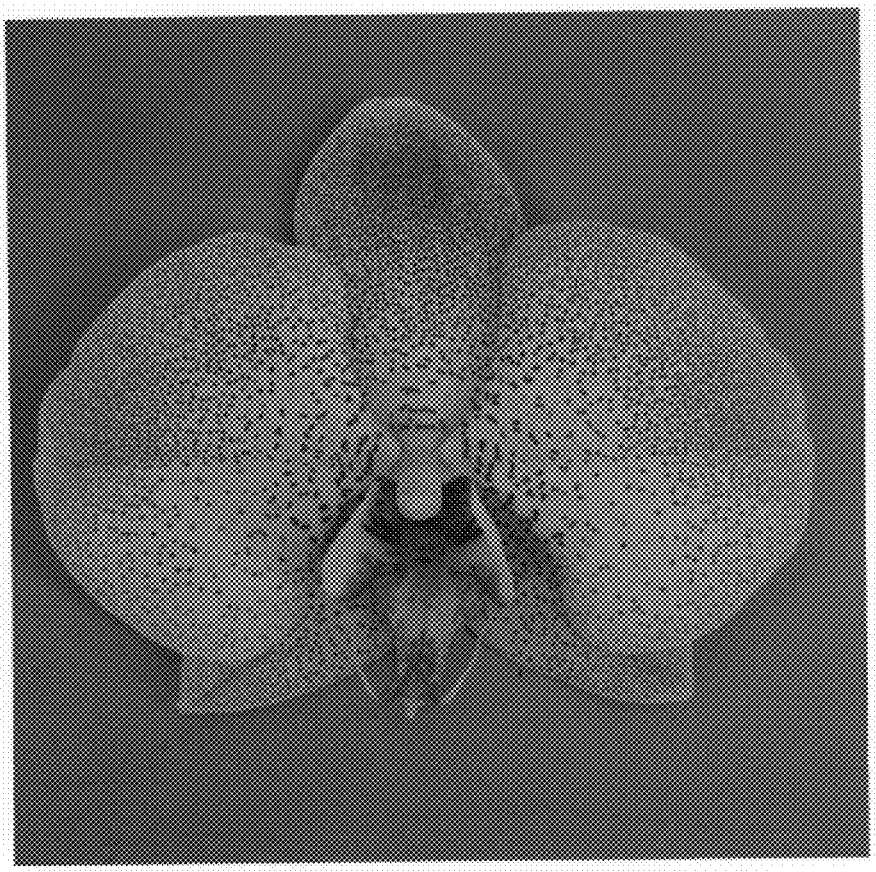
FIG. 2 shows a close-up of a flower of 'PHALDOQZI'.
Figure 3:
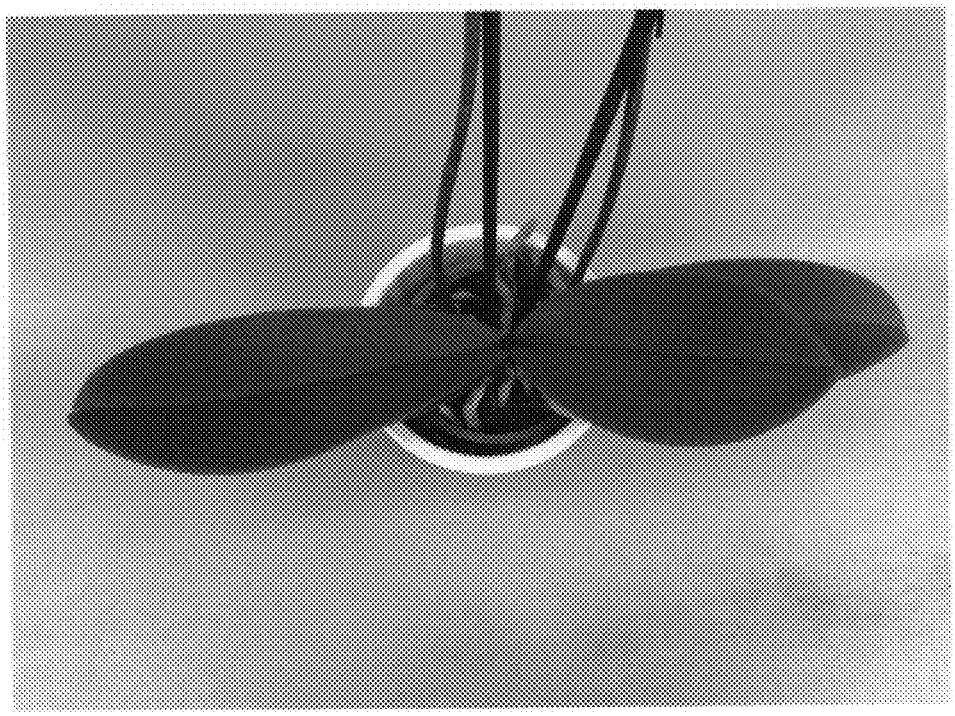
FIG. 3 shows a close-up of the leaves of 'PHALDOQZI'.

The following detailed description sets forth the distinctive characteristics of 'PHALDOQZI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in July 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDOQZI'.

Parentage:

*Female parent*.—*Phalaenopsis* cultivar '01-5021' (unpatented).

*Male parent*.—*Phalaenopsis* cultivar '22884-01' (unpatented).

Propagation:

*Type*.—Meristem tissue culture.

Roots:

*Root description*.—Greyed-green colored roots (RHS 191B/C) with branching lateral roots having red-purple colored root tips (RHS N77A).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 60.0 cm to 65.0 cm.

*Width* (*measured from leaf tips*).—About 36.0 cm to 39.0 cm.

*Vigor*.—Moderate.

Leaves:

*Mature leaves*.—Quantity per plant: 6 to 8 leaves are produced before flowering. Length (fully expanded): 18.5 cm to 20.5 cm. Width: 7.5 cm to 8.5 cm. Shape: Oblong. Base shape: Moderately elongated. Apex: Unequal obtuse. Leaf blade angle with the petiole (measured from the horizontal position): Between 20 degrees and 30 degrees. Leaf margin: Entire. Color: Upper surface: RHS 147A. Lower surface: RHS 147B. Texture: Rough. Thickness: 2.3 mm to 2.5 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—11 to 16.

*Length*.—60.0 cm to 65.0 cm.

*Diameter*.—5.1 mm to 5.3 mm.

*Strength*.—Moderate.

*Aspect*.—Upright to slightly pendant.

*Texture*.—Smooth.

*Color*.—Mix of brown (RHS 200A) and green (RHS 147C).

*Internode length*.—4.0 cm to 4.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 220.0 mm to 260.0 mm.

*Flowering time*.—First flowers can be expected 10 to 11 months after planting in a 12 cm (diameter) pot.

*Flower*.—Height: 83.0 mm to 88.0 mm. Diameter: 97.0 mm to 102.0 mm. Depth of lip: 24.0 mm to 26.0 mm.

*Flower longevity*.—On the plant: 10 to 13 weeks.

*Fragrance*.—Absent.

*Flower bud*.—Average size: Large. Length: 25.0 mm to 27.0 mm. Width: 22.0 mm to 24.0 mm. Shape: Egg shaped. Color: Light green (RHS 145B/C) with diluting purple shade (RHS N79B).

*Petals*.—Arrangement: Open/free. Shape: Semi-circular. Apex: Rounded asymmetric. Margin: Slightly undulated. Length (from base to tip): 46.0 mm to 48.0 mm. Width: 58.0 mm to 60.0 mm. Color (when fully opened): Upper surface: Basic color: White (RHS NN155C). Over color: Slightly light purple shade (RHS 76B) and purple spots (RHS N78B). Lower surface: Basic color: White (RHS NN155C). Over color: Light purple region (RHS 76B) in the middle.

*Dorsal sepal*.—Shape: Elliptic. Apex: Obtuse to rounded symmetric. Margin: Entire. Length (from base to tip): 47.0 mm to 49.0 mm. Width: 31.0 mm to 33.0 mm. Color (when fully opened): Upper surface: Basic color: White (RHS NN155C). Over color: Purple spots (RHS N78B). Lower surface: Basic color: Light purple (RHS 76B). Over color: Light purple region (RHS N78D) in the middle.

*Lateral sepals*.—Shape: Ovate. Apex: Obtuse asymmetric. Margin: Entire. Length (from base to tip): 49.0 mm to 51.0 mm. Width: 29.0 mm to 31.0 mm. Color (when fully opened): Upper surface: Basic color: White (RHS NN155C). Over color: Purple spots (RHS N78B). Lower surface: Basic color: Light purple (RHS 76B). Over color: Light purple (RHS N78D) at the base and toward the tip.

*Labellum* (*lip*).—Whiskers: Present. Length of whiskers: 24.0 mm to 26.0 mm. Color of whiskers: Yellow (RHS 3A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 20.0 mm to 22.0 mm. Width: 16.0 mm to 18.0 mm. Color: White (RHS NN155C) with few dark red stripes (RHS 187B) at the base and yellow (RHS 9B)-brown (RHS 184A) margin on one side.

*Apical lobe*.—Shape: Triangular. Margin: Entire. Length: 22.0 mm to 24.0 mm. Width: 16.0 mm to 18.0 mm. Color: Yellow-orange (RHS 21B and 13C) at the base; white (RHS NN155C) toward whiskers with red-purple spots (RHS 70B).

*Callus*.—Average size: Large. Height: 7.0 mm to 8.0 mm. Length: 6.0 mm to 8.0 mm. Width: 4.0 mm to 6.0 mm. Color: Yellow (RHS 15A) spotted (RHS 178A); light yellow (RHS 12C) on sides.

Reproductive organs:

*Column*.—Length: 8.0 mm to 10.0 mm. Diameter: 5.2 mm to 5.7 mm. Color: Very light purple (RHS 76C) with light purple stripe (RHS 76B) near the tip.

*Pollinia*.—Quantity: 2. Diameter: 0.8 mm to 0.9 mm. Color: Orange (RHS N25A).

*Ovary*.—Length: 7.0 mm to 9.0 mm. Diameter: 2.2 mm to 2.5 mm.

*Pedicel*.—Length: 28.0 mm to 30.0 mm. Diameter: 2.6 mm to 2.9 mm. Color: Green (RHS 147C and 195B) at the base and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALDOQZI', cultivar '01-5021', is no longer in existence, so a meaningful comparison cannot be made.

'PHALDOQZI' differs from male parent plant '22884-01' (unpatented) in that 'PHALDOQZI' has a very light purple column with purple shade and petals with very many dots located on the whole petal, whereas '22884-01' has a white column and petals with many dots located on half of the petal. Additionally, 'PHALDOQZI' has smaller flowers and narrower apical lobes than '22884-01'.

'PHALDOQZI' is most similar to the commercial *Phalaenopsis* plants named 'M369' (unpatented) and 'PHALBOAK' (unpatented). 'PHALDOQZI' differs from the commercial variety 'M369' in that 'PHALDOQZI' has flowers with purple spots and a large callus, whereas 'M369' has flowers with red-purple spots in the center and a medium callus. Additionally, 'PHALDOQZI' has larger flowers and longer whiskers than 'M369'.

'PHALDOQZI' differs from the commercial variety 'PHALBOAK' in that 'PHALDOQZI' has flowers with purple spots and an open arrangement of petals, whereas 'PHALBOAK' has flowers with light purple shade and a touching arrangement of petals. Additionally, 'PHALDOQZI' has larger flowers, longer whiskers and narrower apical lobes than 'PHALBOAK'.

I claim:

1. A new and distinct variety of *Phalaenopsis* plant named 'PHALDOQZI', substantially as described and illustrated herein.

* * * * *